United States Patent [19]
Hassler

[11] Patent Number: 5,374,277
[45] Date of Patent: Dec. 20, 1994

[54] SURGICAL INSTRUMENT

[75] Inventor: William L. Hassler, Sharonville, Ohio

[73] Assignee: Ethicon, Inc., Somerville, N.J.

[21] Appl. No.: 49,724

[22] Filed: Apr. 20, 1993

Related U.S. Application Data

[63] Continuation-in-part of Ser. No. 959,017, Oct. 9, 1992, Pat. No. 5,330,502.

[51] Int. Cl.⁵ .............................................. A61B 17/00
[52] U.S. Cl. .................................... 606/207; 606/170
[58] Field of Search ................ 606/51, 52, 139, 174, 606/205–211; 128/751–755

[56] References Cited

U.S. PATENT DOCUMENTS

| | | |
|---|---|---|
| 4,674,501 | 6/1987 | Greenberg . |
| 4,872,456 | 10/1989 | Hasson . |
| 4,880,015 | 11/1989 | Nierman ............................. 128/751 |
| 5,133,727 | 7/1992 | Bales et al. . |
| 5,133,735 | 7/1992 | Slater et al. . |
| 5,133,736 | 7/1992 | Bales, Jr. et al. . |
| 5,141,519 | 8/1992 | Smith et al. . |
| 5,147,378 | 9/1992 | Markham . |
| 5,152,778 | 10/1992 | Bales, Jr. et al. . |
| 5,156,633 | 10/1992 | Smith . |
| 5,160,343 | 11/1992 | Biancel et al. . |
| 5,170,800 | 12/1992 | Smith et al. . |
| 5,171,256 | 12/1992 | Smith et al. . |
| 5,171,258 | 12/1992 | Bales et al. . |
| 5,174,300 | 12/1992 | Bales et al. . |
| 5,176,702 | 1/1993 | Bales et al. . |
| 5,192,298 | 3/1993 | Smith et al. . |
| 5,196,023 | 3/1993 | Martin . |
| 5,201,743 | 4/1993 | Haber et al. . |
| 5,201,752 | 4/1993 | Brown et al. . |
| 5,211,655 | 5/1993 | Hasson . |
| 5,275,608 | 1/1994 | Forman et al. . |

Primary Examiner—Stephen C. Pellegrino
Assistant Examiner—William W. Lewis
Attorney, Agent, or Firm—Paul A. Coletti

[57] ABSTRACT

Described herein is a minimally invasive surgical instrument comprising an elongate tubular section including a tubular portion and an end effector mount having first and second mount portions and a wrist mechanism associated with the first and second mount portions for permitting adjustment of the angular orientation of the first mount portion relative to the second mount portion. The tubular portion is pivotably connected to a proximal end of the second mount portion. First and second end effectors are further provided and are pivotably connected to a distal end of the first mount portion. Also provided is an actuator mechanism connected to the first and second end effectors for effecting pivotable movement of the first and second end effectors.

16 Claims, 10 Drawing Sheets

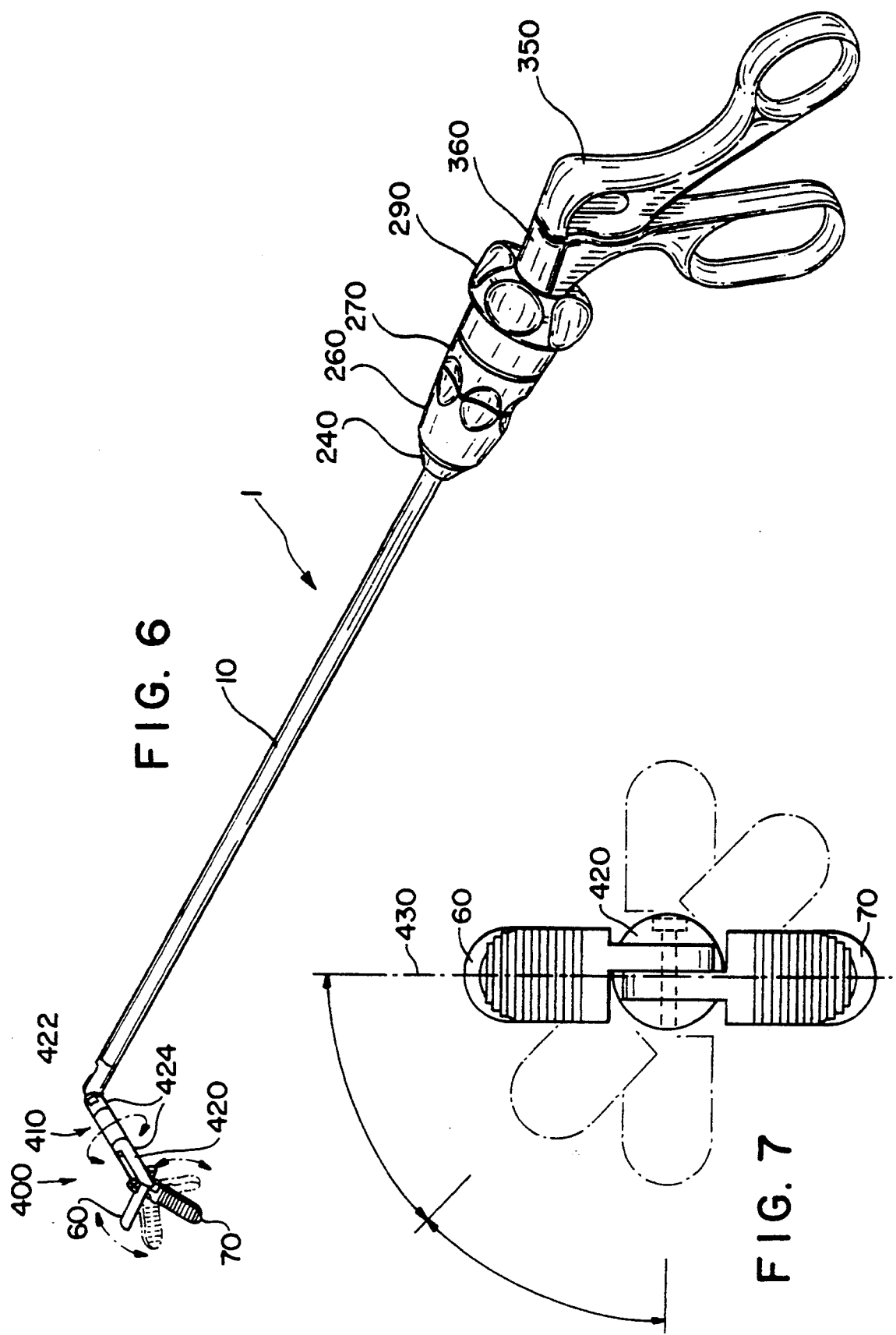

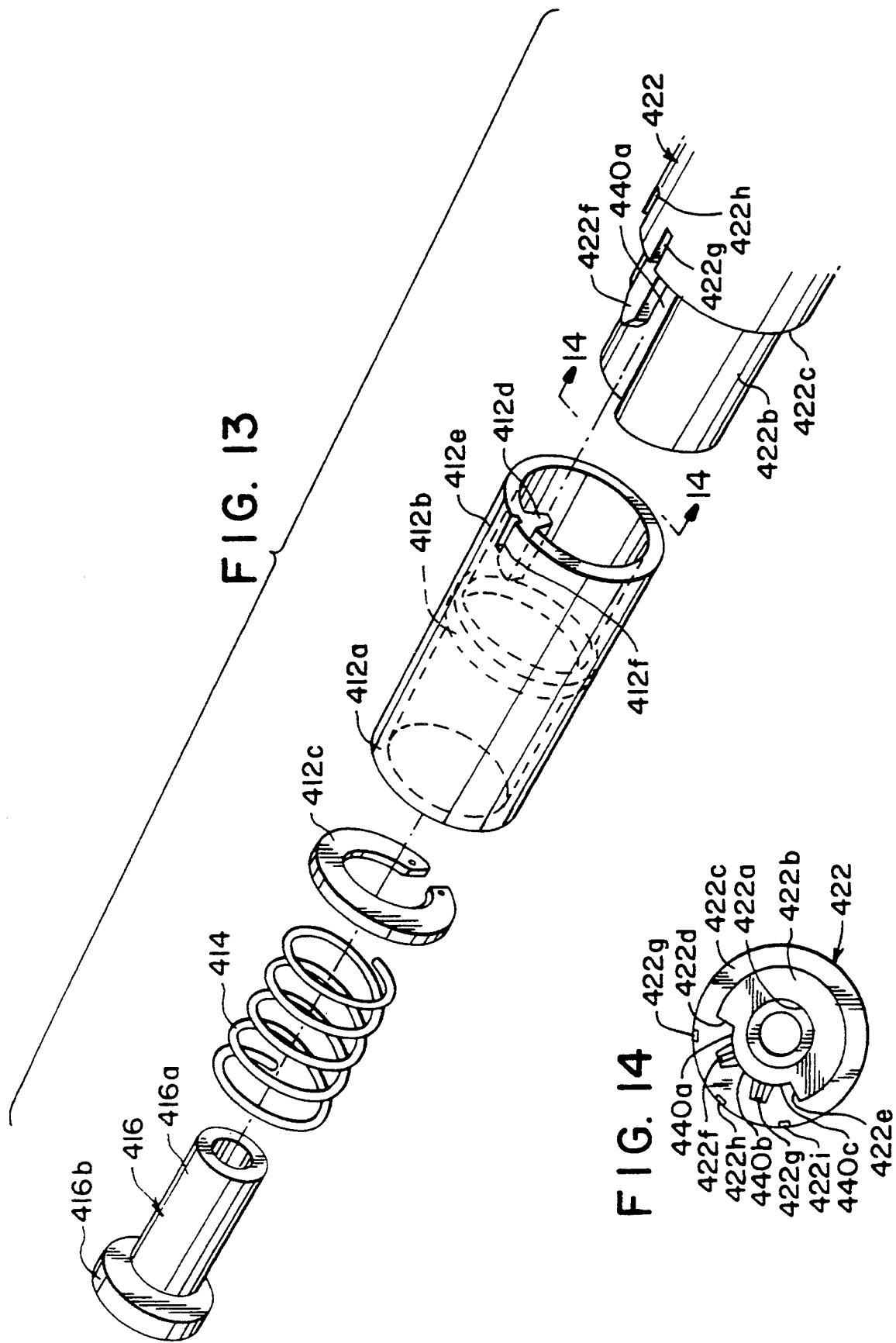

SURGICAL INSTRUMENT

CROSS REFERENCE TO RELATED APPLICATION

This application is a continuation-in-part of U.S. application Ser. No. 07/959,017, filed Oct. 9, 1992, now U.S. Pat. No. 5,330,502 and entitled "Rotational Endoscopic Mechanism with Jointed Drive Mechanism".

FIELD OF THE INVENTION

Generally, this invention relates to minimally invasive surgical instruments. More particularly, this invention relates to minimally invasive surgical instruments having end effectors such as graspers, dissectors, and scissors. Most specifically, this invention relates to minimally invasive surgical instruments having an elongate tubular portion pivotably connected to an end effector portion, wherein the latter includes first and second end effectors and an end effector mount having first and second mount portions and a wrist mechanism associated with the first and second mount portions for permitting adjustment of the angular position of the first mount portion relative to the second mount portion.

BACKGROUND OF THE INVENTION

Within minimally invasive surgery, there is a recognized need for simple devices such as graspers, dissectors, scissors, and other basic surgical instruments. These instruments are necessary in order to perform simple functions during surgical procedures. Specifically, devices such as graspers are necessary in order to properly clear the work site so that the tissue to be worked on may be isolated and surgery may be performed. Scissors may be needed in order to make an appropriate cut in tissue. Dissectors can be necessary to separate one portion of tissue from another. These instruments also enable other, larger instruments, such as staplers and ligating clip appliers, to have sufficient volumetric room to perform effectively during procedures such as appendectomies, cholecystectomies, herniorrhaphies, etc.

Traditionally, minimally invasive surgical instruments such as graspers, dissectors, scissors and the like have been mounted on generally straight shafts. These shafts may or may not have been able to rotate about their longitudinal axes. Nonetheless, there has been perceived a need for the end effector portion of the shaft to be able to angulate with respect to the longitudinal axis of the shaft. This would enable the surgeon to attack tissue to be operated upon from an oblique angle. In fact, it may be desirable to have the shaft angulate up to 90° with respect to the longitudinal axis of the shaft. In many ways, this function can be analogized to the capability of the human hand to rotate around the "axis" of the arm, and also "angulate" about the wrist. Of course, while the hand is able to function with pure rotation, the degrees of freedom given by wrist action are much greater and in many ways enhance the ability of the hand to perform simple daily functions.

Thus, there is perceived a need for a minimally invasive surgical instrument having an end effector portion which is capable of angulating with respect to the longitudinal axis of the instrument. It would additionally be desirable to have an end effector portion which, in addition to being able to angulate with respect to the longitudinal axis of the instrument, includes means for permitting adjustment of the angular position of the end effectors about the central axis of the end effector portion.

SUMMARY OF THE INVENTION

In accordance with a first embodiment of the present invention, a minimally invasive surgical instrument is provided having a shaft which defines a longitudinal axis of the instrument. The shaft extends from a handle portion of the instrument and is able to rotate about the longitudinal axis of the instrument. Such rotation also causes rotation of end effectors, such as scissors or graspers, placed at the distal end of the instrument. Such rotation is effected by rotating a knob placed adjacent the handle portion of the instrument. Grasping or cutting is accomplished by a scissor-like motion of a pair of handles located at the rear of the instrument. One handle is fixed relative to a drive shaft coupled to the end effectors. The other handle is capable of pivoting with respect to the fixed handle. This pivotable movement causes a sliding motion of the drive shaft which is contained within the outer tube of the instrument. A flexible cable is fixedly connected to the drive shaft for movement therewith. This flexible drive cable moves within a clevis and causes operation of the end effectors. In this way, operation of the instrument is accomplished, allowing the surgeon to maintain a stationary hand position.

This instrument also provides for articulation of the end effector portion with respect to the longitudinal axis of the shaft. Articulation is accomplished by operation of front and rear articulating knobs which cause helical grooves or threads to effect linear movement of a winged nut attached to an articulation tube contained in the mechanism. Upon moving, the articulation tube causes the end effector portion to angulate with respect to the longitudinal axis of the outer tube. Depending upon the amount of articulation created by the articulation knob, the outer shaft will angulate from 0° to 90° with respect to the outer shaft of the instrument.

Naturally, once the mechanism has articulated, it is important that the instrument continue to be able to operate. This is accomplished by use of the flexible cable which is coupled to the end effectors and the drive shaft. This flexible cable is capable of operating the end effectors around the angle created by the articulated angulation. Because driving the cable is accomplished around any such angle, the end effectors continue to be able to operate. In this way, use of the device can be made at any angle between 0° and 90° with respect to the longitudinal axis of the shaft.

A locking mechanism is provided which prevents articulation during rotation of the shaft and the end effector portion. In this way, during rotational motion, the means for effecting articulation is held in place, and there is no articulation of the end effector portion with respect to the longitudinal axis of the instrument. In contrast, during articulation, the rotational mechanism is locked in place so that the relative rotational position is maintained. This "clutch-type" mechanism allows the user to accomplish many varied functions during a surgical procedure.

In accordance with a further embodiment of the present invention, a surgical instrument is provided having an elongate tubular or shaft section, first and second end effectors, and actuator means connected to the first and second end effectors for effecting pivotable movement of the first and second end effectors. The elongate tubular section includes a tubular or shaft portion and an end effector mount. The tubular portion comprises an outer tube and an elbow fixedly connected thereto. The end effector mount includes first and second mount portions and wrist means associated with the first and second mount portions for permitting adjustment of the angular orientation of the first mount portion relative to the second mount portion. The tubular portion is pivotably connected at its elbow to a proximal end of the second mount portion. The first and second end effectors are pivotably connected to a distal end of the first mount portion. When the angular orientation of the first mount portion is adjusted via the wrist means, the angular orientation of the first and second end effectors is likewise changed.

The wrist means preferably comprises an outer tube, a spring retention pin and a spring. The outer tube is fixedly connected to a proximal end of the first mount portion. It includes an internal spring engagement member and a position engagement tooth. The spring retention pin is positioned within the outer tube and includes a sleeve portion and a spring contact portion. The sleeve portion is fixedly mounted within a bore in a distal end of the second mount portion. The spring is positioned about the sleeve portion of the spring retention pin and is interposed between the internal spring engagement member and the spring contact portion for biasing a proximal end of the outer tube toward the distal end of the second mount portion.

At least first and second recesses are formed within the distal end of the second mount portion and are spaced circumferentially apart from one another about the distal end of the second mount portion. The outer tube is rotatable about its central axis between a first position where the position engagement tooth engages with the first recess and a second position where the position engagement tooth engages with the second recess.

The various embodiments of the present invention will be better understood in relation to the attached drawings taken in conjunction with the detailed description of the invention.

DETAILED DESCRIPTION OF THE DRAWINGS

FIG. 6 is a perspective view of a surgical instrument constructed in accordance with a second embodiment of the present invention;

FIG. 7 is an end view of the end effector portion of the instrument shown in FIG. 6 wherein the end effectors are shown in a first angular position and are further shown in phantom in two additional angular positions;

FIG. 13 is an exploded view of the wrist of the instrument illustrated in FIG. 6; and FIG. 14 is a view taken along line 14—14 in FIG. 13.

DETAILED DESCRIPTION OF THE INVENTION

Figure 1:
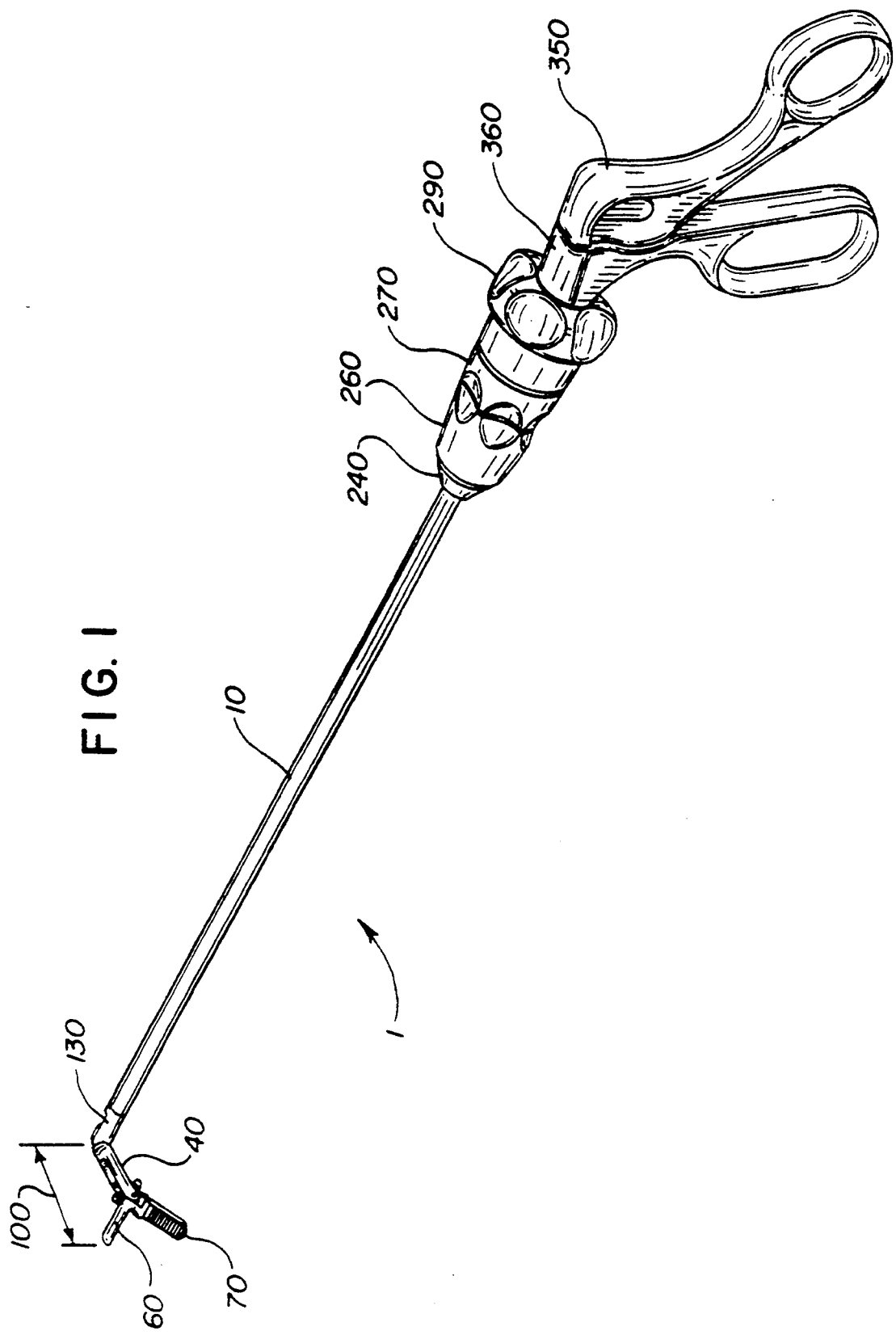
FIG. 1 is a perspective view of a minimally invasive surgical instrument constructed in accordance with a first embodiment of the present invention.
Figure 4:
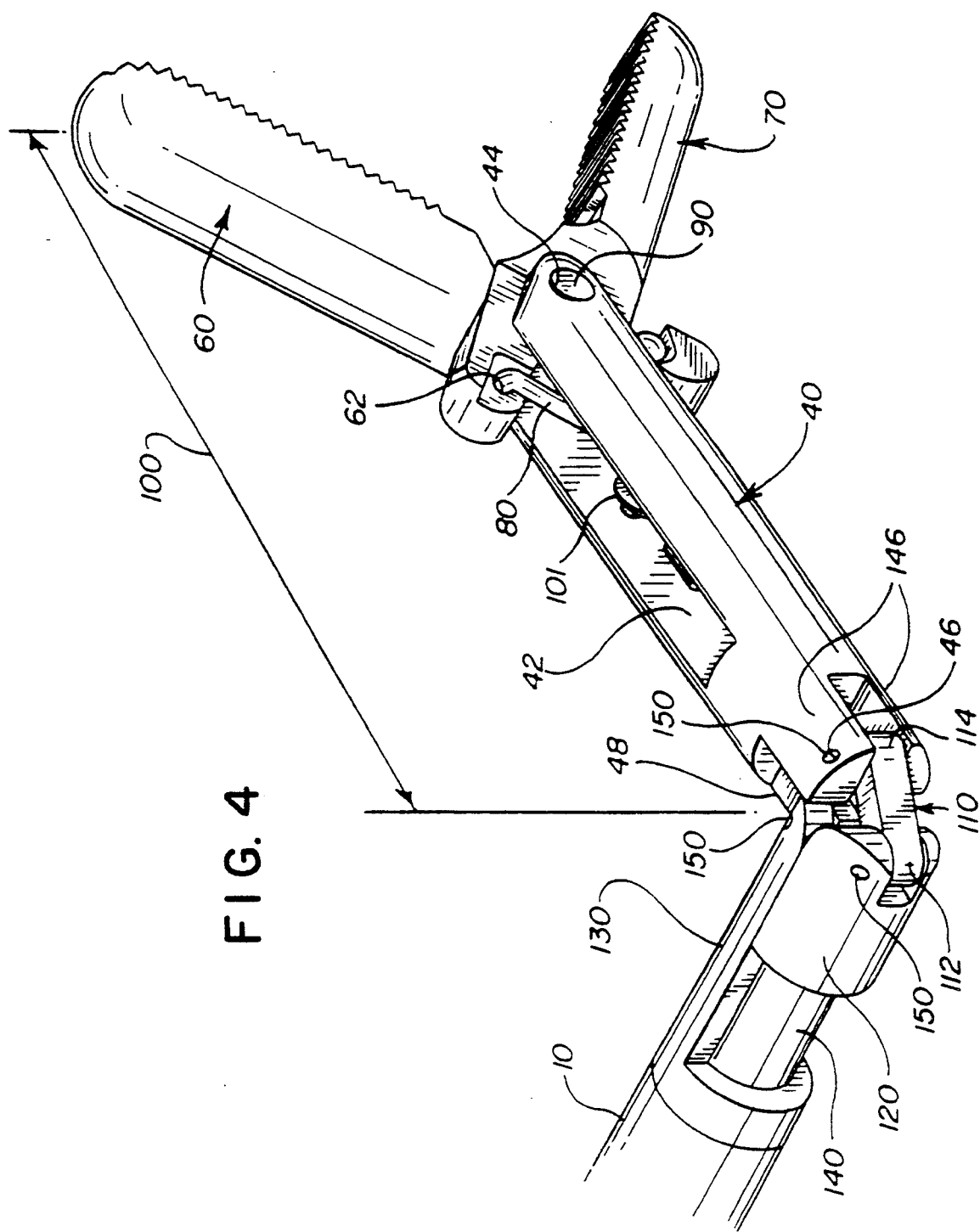
FIG. 4 is a perspective view of the articulated end of the instrument shown in FIG. 1.

An instrument 1 for performing minimally invasive surgical procedures, constructed in accordance with a first embodiment of the present invention, is described herein and is seen generally in FIG. 1. This instrument 1 includes an end effector portion 100 which is capable of rotating about the longitudinal axis of the shaft or outer tube 10, which axis defines the longitudinal axis of the instrument 1. As well, end effector portion 100 is capable of being angulated so that it may be placed at an angle up to 90° with respect to the longitudinal axis of the shaft 10, as best shown in FIG. 4.

Figure 2:
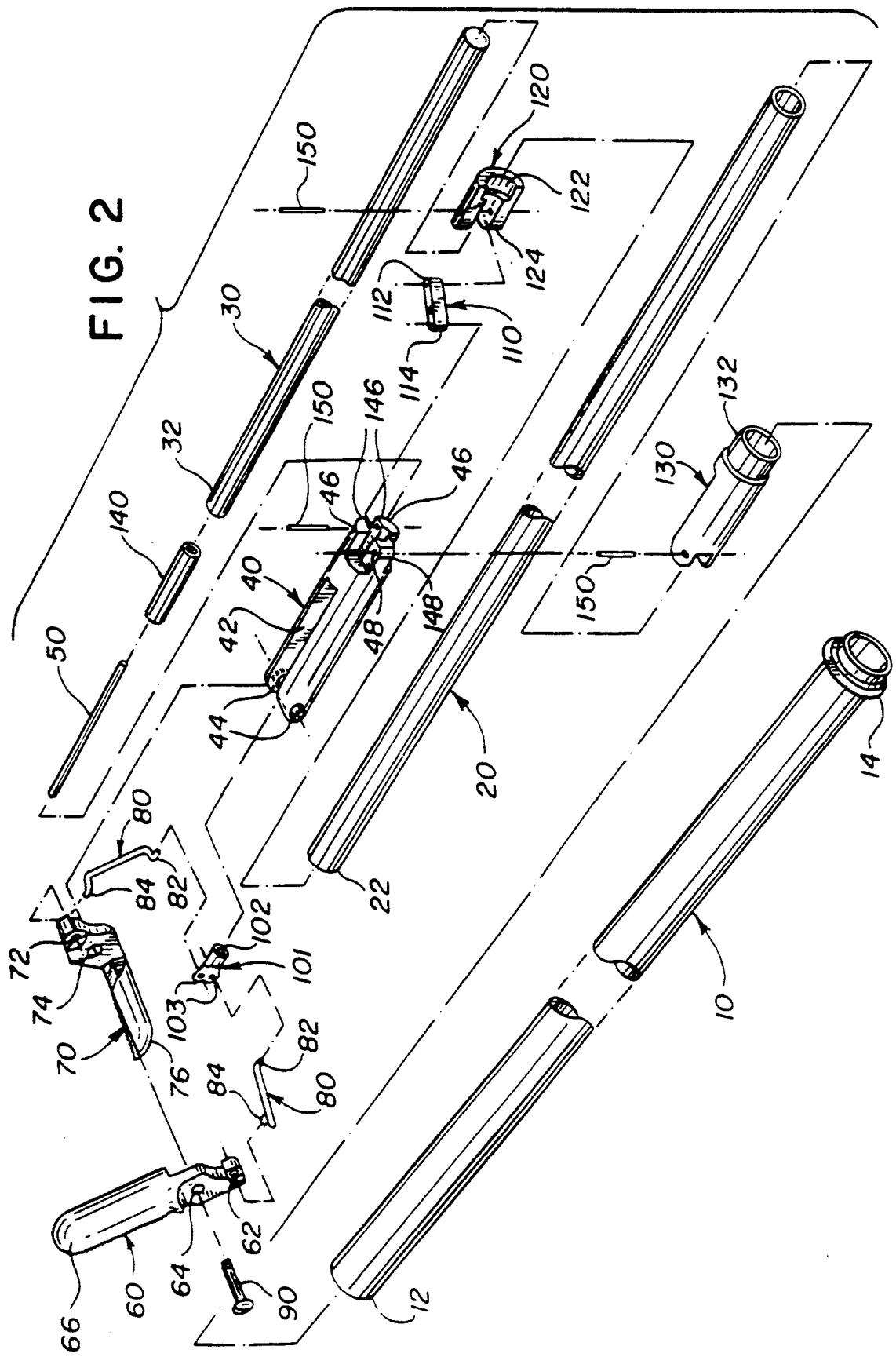
FIG. 2 is an exploded assembly view illustrating the end effector portion, the outer tube, the articulation tube and the drive rod of the instrument shown in FIG. 1.

As shown in FIG. 2, the instrument 1 includes a drive rod 30 which is generally cylindrical and runs substantially the entire length of the instrument 1. This drive rod 30 is positioned within an articulation tube 20. The articulation tube 20 is also cylindrical and is able to be moved longitudinally with respect to the drive rod 30. Further, the articulation tube 20 and the drive rod 30 fit within the outer tube 10 of the instrument 1. While tubes 10 and 20 are shown in the illustrated embodiment as having a generally circular cross-section, they may have any geometric cross-section desired for a given application or for appearance purposes. Rod 30 may also be formed to have any reasonable cross-section; however, rod 30 typically would have the same cross-section as the tube 20.

The driving portion of the instrument 1 and its end effectors will now be described. The drive rod 30 is capable of moving longitudinally with respect to the outer tube 10. This drive rod 30 is connected at its distal end to a drive cable 50 at crimp 32. This drive cable 50 fits securely within a cable sleeve 140. At the distal portion of the drive cable 50, there is attached a rod end 101 via solder and crimping at end 102. This rod end 101 is capable of effecting pivotable movement of end effectors 60 and 70. The rod end 101 is held within the longitudinal center 42 of the clevis 40. The drive cable 50 also fits securely within the center 42 of the clevis 40 and both the rod end 101 and drive cable 50 are capable of moving with respect to the clevis 40.

When the drive cable 50 is moved with respect to the clevis 40, it guides the rod end 101 in a longitudinal fashion with respect to the clevis 40. In so doing, the rod end 101 pivots the pair of jaw links 80. These jaw links 80 rotate at the rod end 101 at pivot points 103. As best shown in FIG. 2, the jaw links 80 include flared ends 82, which extend outwardly from the central axis of the drive rod 30.

At the distal ends of the rod links 80 are attached the end effectors of the instrument. For instance, in this example, there are shown end effectors which comprise an upper jaw 60 and a lower jaw 70 of a grasping mechanism. However, it is to be understood that these end effectors may be scissors or dissectors or other surgical instruments. What is necessary is that the end effectors 60, 70 are attached at their respective proximal ends 62, 72 to the distal ends 84 of the jaw links 80, in order that the jaw links 80 may move the end effectors 60, 70.

Thus, when the drive rod 30 is moved in a proximal fashion toward the user, the drive cable 50 is similarly pulled in a proximal direction. This drive cable 50 is capable of pulling the rod end 101 so that it too moves in a proximal direction. Because the jaw links 80 are connected to the rod end 101 at the pair of pivoting points 103, the jaw links 80 are similarly pulled in a proximal direction. In this manner, the jaw links 80 rotate from an outwardly flared position to an inwardly flared position with respect to the longitudinal axis of the drive rod 30. When this occurs, the jaw links 80 at their distal ends rotate the proximal ends of the end effectors 60, 70 toward the longitudinal axis of the instrument. The end effectors 60, 70 are pivoted at points 64, 74 about shoulder screw 90 attached to pivot holes 44 contained at the distal end of the clevis 40. Thus, the end effectors 60, 70 similarly rotate about the clevis 40 so that the entire mechanism is "closed".

On the other hand, when the drive rod 30 is pushed distally, the rod end 101 causes the jaw links 80 to flare outwardly from the longitudinal axis of the drive rod 30. This outward flaring causes the ends 66, 76 of the end effectors 60, 70 to similarly move outwardly. The end effectors 60, 70 pivot at points 64, 74 about shoulder screw 90 connected to the pivot holes 44 at the end of clevis 40. Thus, with this rotation, the end effectors 60, 70 also pivot so that the device is now "open". In this fashion, therefore, reciprocal motion of the drive rod 30 operates the end effectors 60, 70 of the instrument 1.

It is to be understood that the drive rod 30 is capable of moving with respect to both the articulation tube 20 and the outer tube 10 of the instrument 1. In this fashion, motion of the drive rod 30 is capable of being performed regardless of the relative positioning of either the articulation tube 20 or the outer tube 10. Thus, the motion of the drive rod 30 is capable of causing performance of the end effectors 60, 70 at any rotational position of the instrument 1.

Articulation of the end effector portion 100 will now be described. This articulation can best be understood from observing motion of the articulation tube 20 in relation to the outer tube 10 of the mechanism. The articulation tube 20 is connected by a weld at its distal end 22 to the internal chamber 122 of slider elbow 120. The distal end 12 of the outer tube 10 fits over the smaller outer circumference 132 contained at the proximal end of fixed elbow 130 and is rigidly connected thereto. The slider elbow 120, therefore, is able to move with respect to the outer tube 10 along the longitudinal axis of the instrument 1. This can be seen in FIGS. 1 and 4, for instance. There, the articulation tube 20 has moved distally. Similarly, the slider elbow 120 has been moved distally by the articulation tube 20. As will be further discussed below, this sliding motion causes the angulation of the end effector portion 100 of the instrument 1.

The distal end 124 of the slider elbow 120 is connected by a pin 150 to the proximal end 112 of the elbow link 110. This elbow link 110 is connected by a similar pin 150 at its opposite or distal end 114 to pivot holes 46 on tabs 146 of clevis 40. Similarly, the clevis 40 is connected by pin 150 at pivot hole 48 on an opposite tab 148 to the fixed elbow 130. With these connections arranged in this fashion, angulation of the end effector portion 100 with respect to the longitudinal axis of the instrument can be accomplished. Thus, when the articulation tube 20 is moved distally, the slider elbow 120 is also moved distally. This distal movement of the slider elbow 120 causes rotation of the elbow link 110 about the proximal end 112 connected to slider elbow 120. Such motion similarly causes motion of the elbow link 110 about distal end 114 connecting elbow link 110 and clevis 40. However, because the clevis 40 is fixed at tab 148 to the fixed elbow 130 connected to the outer tube 10, the clevis 40 is caused to rotate relative to the longitudinal axis of outer tube 10, in the manner of a typical four-bar linkage.

This can best be seen in FIG. 4, where motion has been accomplished. There, it is seen that the distal motion of the slider elbow 120 has caused angulation of the clevis 40 from the longitudinal axis of the outer tube 10. Of course, proximal motion of the slider elbow 120 caused by proximal motion of the articulation tube 20 causes return rotation of the clevis 40 to a position where there is no angulation between the clevis 40 and the longitudinal axis of the outer tube 10.

It is desirable to accomplish operation of the instrument 1 at any angulation of the clevis 40 with respect to the outer tube 10. Thus, it is important for the drive rod 30 to be able to move with respect to the clevis 40 at any angular position of the clevis 40. This is accomplished through the attachment of the drive rod 30 to the drive cable 50. Because the drive cable 50 is flexible, it can move with respect to the clevis 40 when the clevis 40 is positioned at an angle to the outer tube 10, the articulation tube 20 and the drive rod 30. A portion of the drive cable 50 extends through a cable sleeve 140 made from a low friction material such as Teflon TM, and therefore motion of the drive cable 50 within the clevis 40 is readily accomplished. The cable sleeve 140 may alternatively comprise a wire-wound guide sleeve (not shown).

Thus, motion of the drive cable 50 can be accomplished at any angular position of the clevis 40 with respect to the outer tube 10, even at 90° angles, which has heretofore not been possible for any articulating type minimally invasive surgical instruments.

Figure 3:
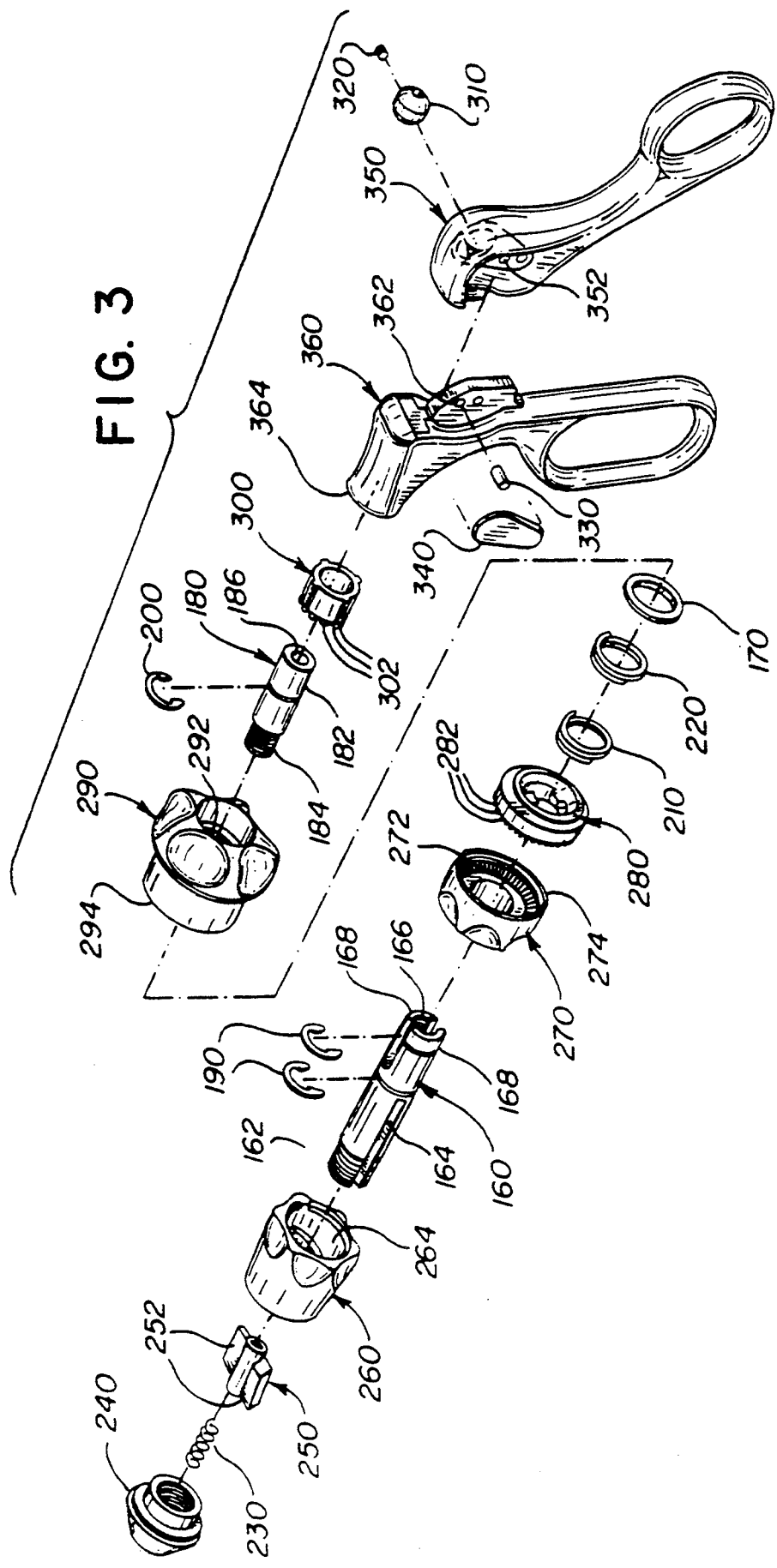
FIG. 3 is an exploded assembly view of the handle portion of the instrument shown in FIG. 1.
Figure 5:
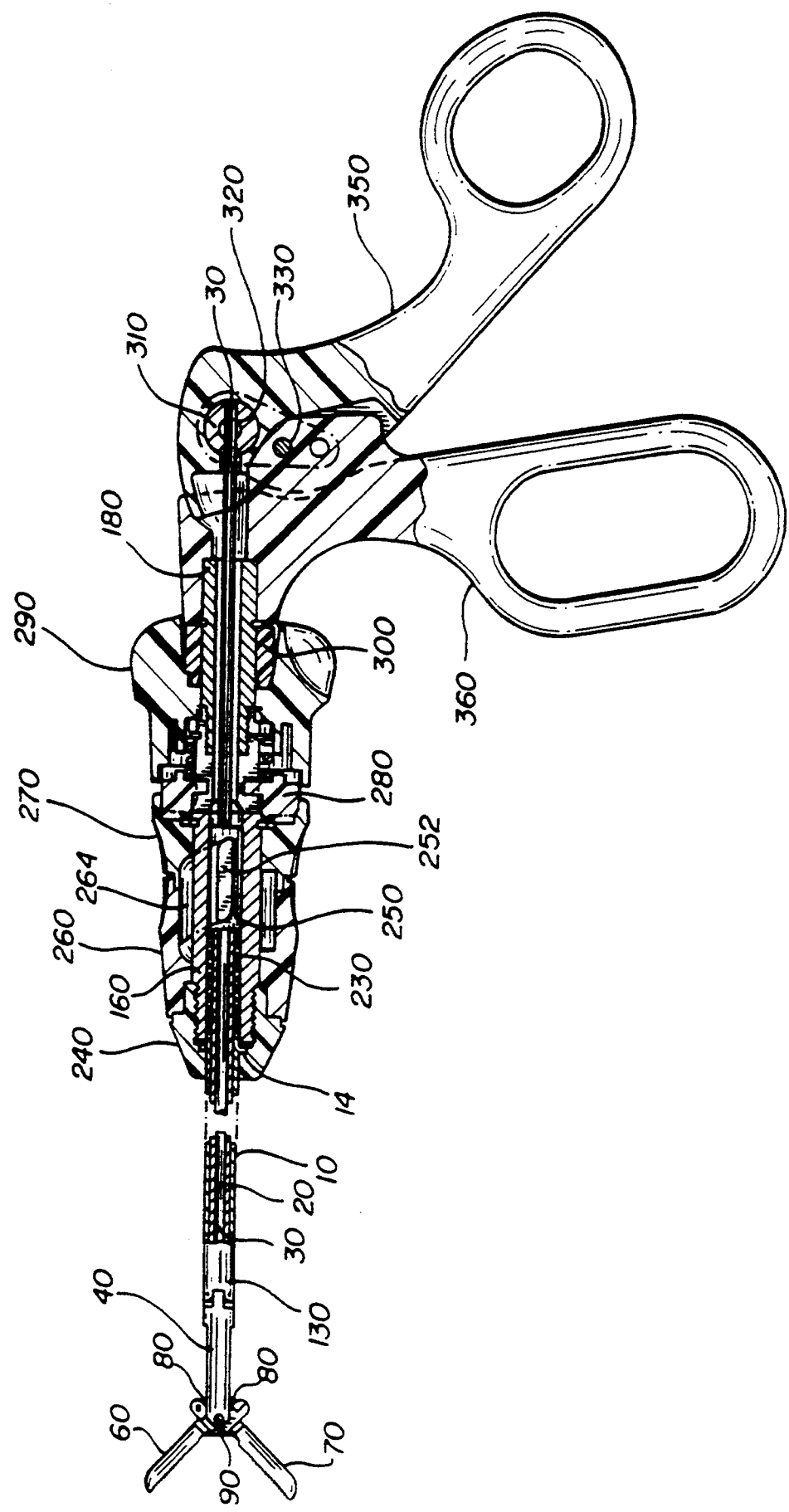
FIG. 5 is a partial cross-sectional side view of the instrument shown in FIG. 1.
Figure 8:
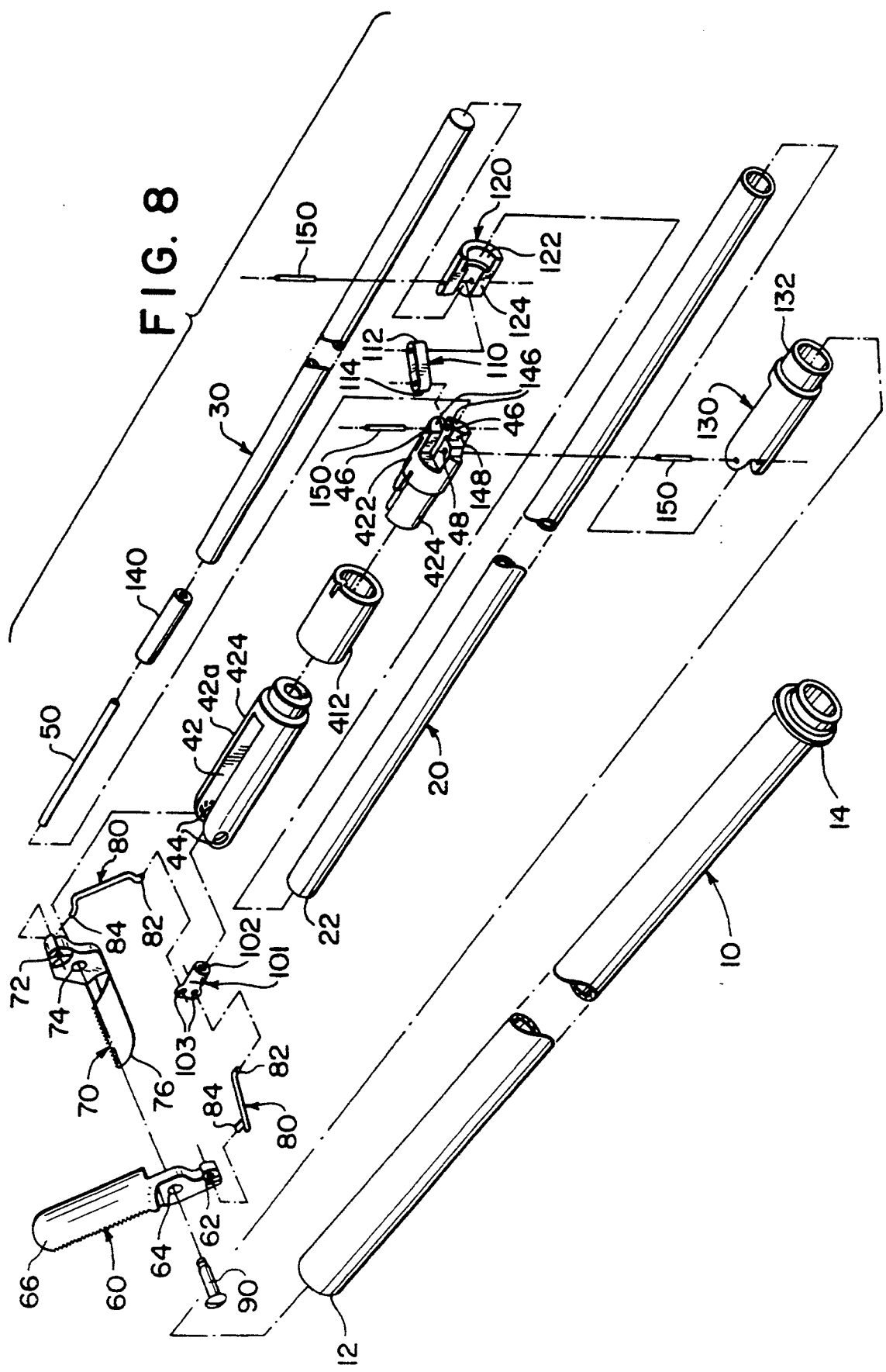
FIG. 8 is an exploded assembly view illustrating the end effector portion, the outer tube, the articulation tube and the drive rod of the instrument shown in FIG. 6.
Figure 9:
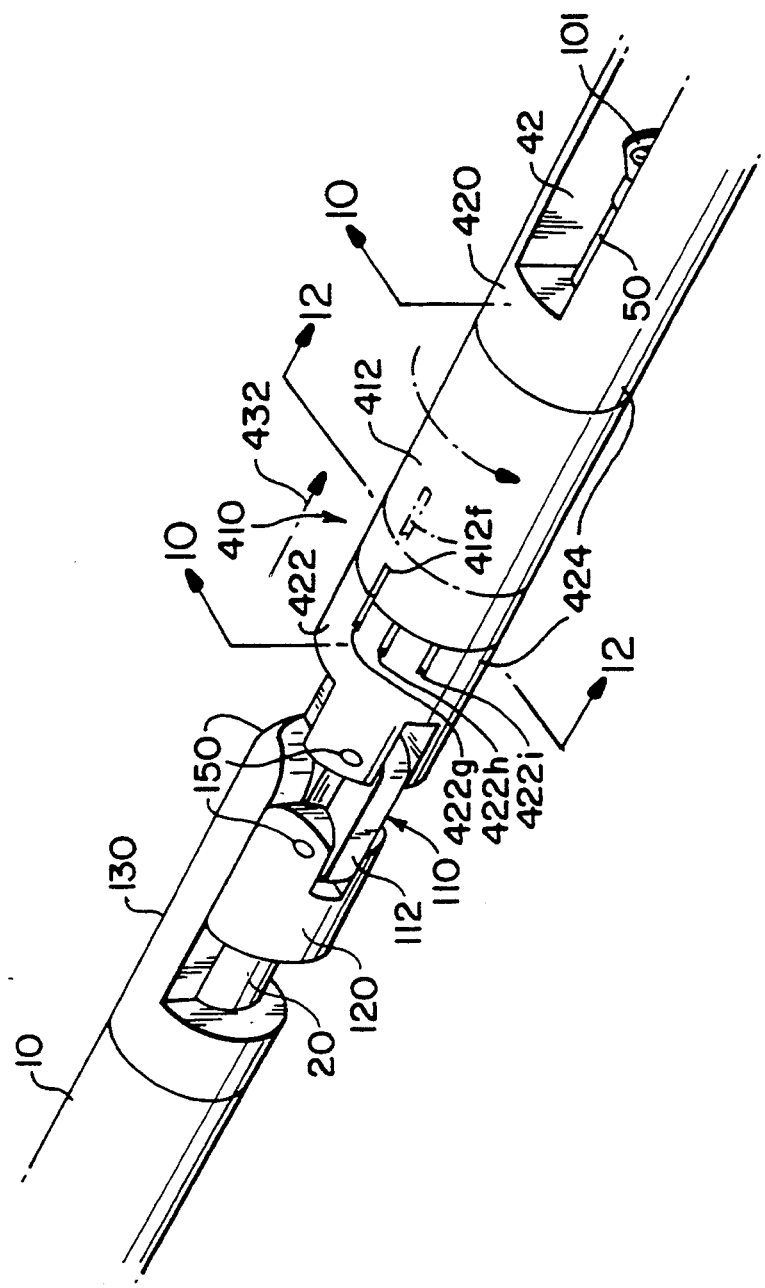
FIG. 9 is a perspective view of the wrist of the instrument shown in FIG. 6.
Figure 10:
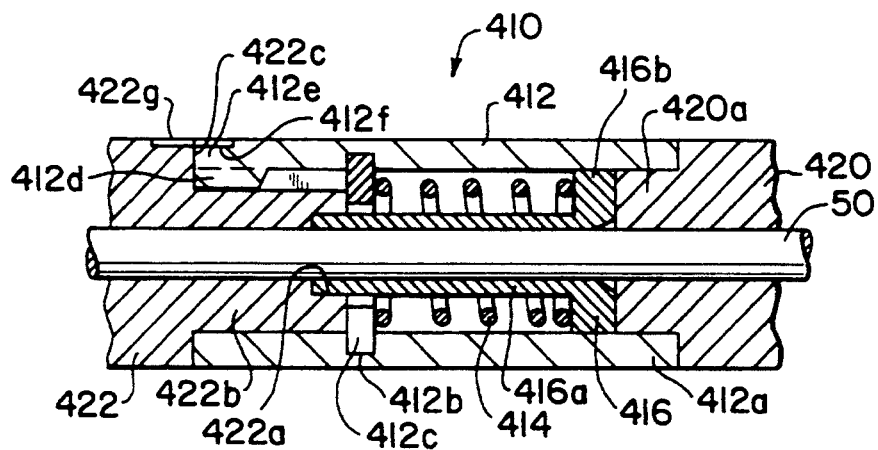
FIG. 10 is a view taken generally along section line 10—10 in FIG. 9.
Figure 11:
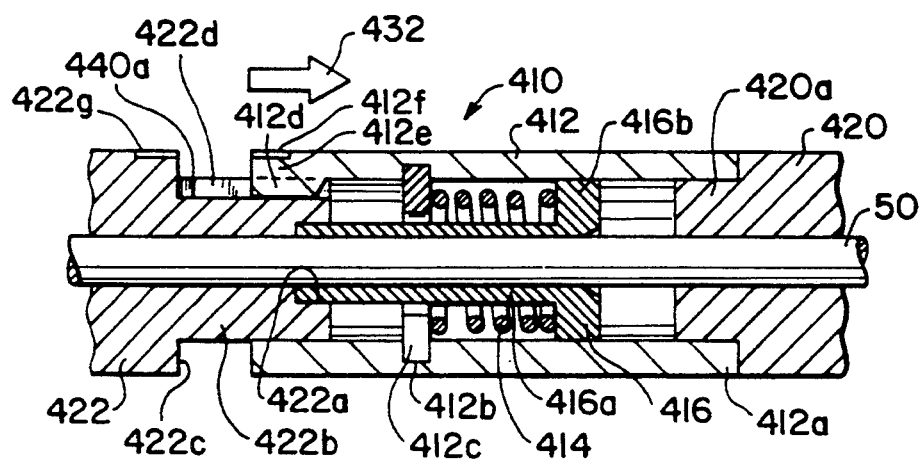
FIG. 11 is a cross-sectional view similar to FIG. 10, but showing the outer tube of the wrist displaced from the distal end of the second mount portion.
Figure 12:
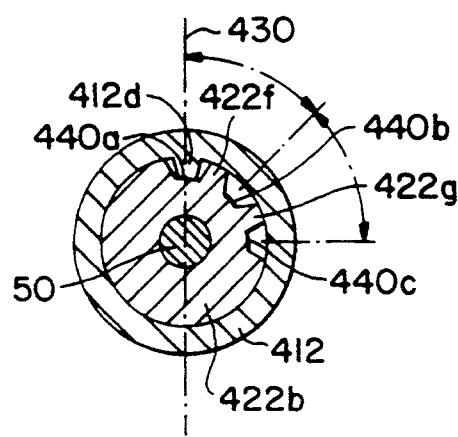
FIG. 12 is a cross-sectional view taken generally along section line 12—12 in FIG. 9.

Now that the end effector 100 portion of the instrument has been described, this instrument 1 must be understood in conjunction with the control portion of the instrument 1. It must be remembered that while articulation and operation of the end effectors 60, 70 are accomplished, only three portions extend into the handle. That is, only the outer tube 10, the articulation tube 20, and the drive rod 30 extend into the handle section of the instrument 1. Importantly, it is to be noted that the outer tube 10 is connected via its flange 14 to the end cap 240 which is positioned adjacent to the front of articulation knob 260 of the instrument 1. This can best be seen in FIGS. 3 and 5. The articulation tube 20 is press fit or otherwise connected to the wing nut 250, see FIG. 5, so that motion of wing nut 250 causes motion of tube 20. The drive rod 30 extends through the entire instrument 1 and is connected at its proximal end to the drive ball 310, which is maintained within the trigger 350 contained at the proximal end of the instrument 1. This drive ball 310 is secured by set screw 320 to drive rod 30.

The trigger 350 is capable of rotating about the handle 360 of the instrument via a pin 330 which connects both the handle and the trigger at pivot holes 352, 362. This pill 330 is held in place by a trigger cover 340 as better seen in FIG. 3. Thus, it will be readily understood that the driving of the end effectors 60, 70 of this instrument is accomplished solely by the scissoring action of the trigger 350 with respect to the handle 360. When the trigger 350 is rotated so that it is closer to the handle 360, the drive ball 310 is caused to pivot proximally with respect to the handle 360. This proximal motion of the drive ball 310 causes proximal motion of drive rod 30, and consequently causes a closing of the end effectors 60, 70 one on the other. The motion of the trigger 350 away from the handle 360 causes pivoting about pin 330 so that there is caused a distal motion of the drive rod 30. In this way, a distal motion at the distal end 32 of the drive rod 30 results, causing the end effector jaws 60, 70 to move away from one another, and therefore accomplish opening of scissors or graspers or any other surgical end effectors.

This driving capability of the instrument 1 must now be understood in conjunction with the articulation or angulation described above, taken further in conjunction with rotation of this instrument 1. First, the articulation aspects of this instrument will be described. Articulation is accomplished by the articulation knob assembly, which comprises the front articulation knob 260 and the rear articulation knob 270, which knobs 260, 270 are fixedly secured to one another. Positioned within this articulation knob assembly and fitted within slot 164 of double slotted tube 160 is the articulation wing nut 250. The slotted tube 160 is screwed at threads 162 to cap 240. A spring 230 regulates motion of the articulation wing nut 250 within the slot 164. The articulation wing nut 250 is connected to the articulation drive tube 20, as described above. Accordingly, movement of the articulation wing nut 250 causes the drive tube 20 to move the end effectors 60, 70 and clevis 40 at the distal end of the instrument 1. Of course, because the outer tube 10 is connected at flange 14 to the end cap 240, when articulation is accomplished, the articulation tube 20 is capable of moving with respect to the outer tube 10.

When it is desired to perform articulation, the user rotates the articulation knob assembly. In this way, the inner helical thread or groove 262 of the front articulation knob 260 and the inner helical thread or groove 270a of the rear articulation knob 270, see FIG. 5, cause relative motion between wings 252 of the articulation wing nut 250 and the remainder of the instrument 1. In other words, with a clockwise motion, the articulation wing nut 250 is pulled proximally toward the user. In this way, the articulation tube 20 similarly moves proximally, and therefore slider elbow 120 is also moved proximally. This tends to straighten the clevis 40 with respect to the longitudinal axis of the outer tube 10 of the instrument 1. Conversely, when the knobs 260, 270 are moved counterclockwise, the helical grooves 262,270a of knobs 260, 270 cause the articulating wing nut 250 to move distally within slot 164. This distal motion causes distal motion of the slider elbow 120, and in turn causes angulation of the clevis 40 with respect to the longitudinal axis of the outer tube 10.

Helical grooves 262 and 270a convert the rotary motion of the knobs 260, 270 into linear motion of the articulation tube 20. This rotary motion gives a generally one-to-one ratio between motion and articulation. Thus, roughly 120° of knob rotation is needed for 90° of shaft articulation. Thus, the user is able to get a general "feel" for angulation of clevis 40 over a relatively easy (from the user's perspective) length of motion.

Next, it will be necessary to describe rotational motion of this instrument 1. However, in order to do so, it will first be necessary to understand the interrelationship between the articulation portion of the instrument 1 and the rotational portion of the instrument 1. Generally, as can be seen from the figures, rotation spring 220 causes the rotation knob 290 to be moved proximally within the instrument 1. This rotation knob 290 has contained within it a series of locking ratchets 292. These locking ratchets 292 are capable of mating with the ratchets 302 of rotational lock 300. The rotational lock 300 is adhesively secured within opening 364 in the handle 360. Positioned within the opening 364 at the proximal end of the lock 300 is a retaining ring 200, which serves to secure tube 180 in place within the opening 364 in the handle 360, see FIG. 5.

When the rotation spring 220 pushes on the rotation knob 290, it causes the locking ratchets 292 on the rotation knob 290 to mate with the rotation lock ratchets 302, so that the rotation knob 290 is statically held with respect to the handle 360. Thus, typically when the user rotates articulation knobs 260, 270, this causes motion of the articulation wing nut 250 and its concomitant articulation tube 20 with respect to the stationary outer tube 10, the end cap 240, the stationary handle 360, the trigger 350, and the rotation knob 290.

Interposed between the rear articulation knob 270 and the rotation knob 290 is articulation ratchet lock 280. It includes a series of knurls 282 which interact with knurls 272 contained in the proximal portion 274 of the rear articulation knob 270. Extending through the center of rotation knob 290 is the tube 180. This tube 180 is held within fixed handle 360 by the retaining ring 200, as described above. The tube 180 has threads 184 on its distal end which are matedly threaded within the threads 166 of the slotted tube 160 so as to be fixedly secured thereto. The articulating knobs 260, 270 are free to rotate with respect to the handle 360 and, therefore, the articulation wing nut 250 is capable of moving with respect to the handle 360/trigger 350 combination. The drive tube 30 is extended through the center 186 of the approximately 10 mm tube 180 and into the handle 360 as previously described.

An articulation spring 210 is placed between articulation ratchet lock 280 and spring retainer 170. Together, the articulation ratchet lock 280, the spring 210 and the spring retainer 170 are positioned between the snap rings 190. The rear articulation knob 270 is located on the distal side of the distal-most snap ring 190 and is prevented from moving proximally by that snap ring 190. The articulation spring 210, which is stiffer than the rotation spring 220, causes the knurls 282 on the free floating articulation ratchet lock 280 to engage with the knurls 272 on the rear articulation knob 270. Thus, when the rotation knob 290 is engaged with the lock 300 and the articulation knobs 260, 270 are rotated with respect to the stationary rotation knob 290, the articulation knob 270 moves relative to stationary ratchet lock 280 so that its knurls 272 slip over the knurls 282 on the ratchet lock 280. The rotation spring 220 is positioned between the articulation ratchet lock 280 and the rotation knob 290 for urging the rotation knob 290 into engagement with the rotation ratchet lock 300, see FIG. 5.

When it is desired to rotate the tubes 10, 20 and drive rod 30 with respect to the handle 360, the user places a distal force on the rotation knob 290 and rotates same. Distal force on the rotation knob 290 causes the locking ratchets 292 on the rotation knob 290 to disengage with the rotation lock ratchets 302 on the lock 300. The rotation knob 290 is provided with two ears 290a, see FIG. 5, which extend into the slots 168 on the slotted tube 160, even when the knob 290 is engaged with lock 300. The ratchet lock 280 also includes ears 280a which extend into the slots 168 on the slotted tube 160. Upon disengagement of the locking ratchets 292 with the lock ratchets 302 and rotation of the rotation knob 290, the slotted tube 160 is rotated which, in turn, causes rotation of the articulation wing nut 250 and its concomitant articulation tube 20, the end cap 240 and the outer tube 10, and the ratchet lock 280. Rotation of the ratchet lock 280 effects rotation of the articulation knobs 260 and 270 due to engagement of knurls 272 with knurls 282. Thus, the distal motion of the rotation knob 290 causes a "locking-up" of the entire rotational mechanism. In this way, rotation of the rotation knob 290 causes rotation of the slotted tube 160 which, in turn, causes rotation of the end cap 240 and the outer tube 10 as well as rotation of the wing nut 250 and the articulation tube 20. This rotation further causes simultaneous rotation of the fixed elbow 130, the clevis 40 and the end effectors 60, 70.

Because the end effectors 60, 70 are connected via the drive cable 50 to the drive rod 30, this causes rotation of the drive rod 30 within the entire mechanism. (Normally, it is to be remembered that the drive rod 30 moves independently of the articulation tube 20 and the outer tube 10.) Rotation of the drive tube 30 causes rotation of the ball 310 within the handle 360. Thus, orientation of the drive rod 30 now is effected within the handle 360. However, as the trigger 350 is able to cause motion of the drive rod 30 at any rotational position of the drive rod 30, utility of the handle 360/trigger 350 combination is not effected.

An end effector portion 400, constructed in accordance with a second embodiment of the present invention, will now be described with reference to FIGS. 6–14, where like elements are referenced by like numerals. In this embodiment, the end effector portion 400 includes an end effector mount 424 and first and second end effectors 60 and 70, which are pivotably connected to a distal end of the mount 424. The end effector mount 424 is provided with a three-position wrist 410 and first and second mount portions 420 and 422 which are associated with the wrist 410, see FIG. 6. As will be more explicitly set out below, by rotating the wrist 410, the end effectors 60 and 70 are rotated about the central axis of the end effector portion 400 between first, second and third positions, which are located at angles of 0°, 45° and 90° respectively, to an axis 430 shown in FIG. 7. The rotation of the end effectors 60 and 70 about the central axis of the end effector portion 400 is independent of rotation of the tubes 10, 20 and the drive rod 30 with respect to the handle 360 effected by turning the rotation knob 290.

Referring now to FIGS. 10–13, the wrist 410 comprises an outer tube 412, a spring 414 and a spring retention pin 416. The distal end 412a of the outer tube 412 is press fit onto or otherwise fixedly secured to an extension 420a at the proximal end of the first mount portion 420. The outer tube 412 includes an internal spring engagement member which, in the illustrated embodiment, comprises a snap ring 412c located within an internal circumferential recess 412b in the outer tube 412. In place of the snap ring 412c, the outer tube 412 may be formed having an integral shoulder (not shown) which functions as the internal spring engagement member. The outer tube 412 further includes an internal position engagement tooth 412d.

The spring retention pin 416 is positioned within the outer tube 412 and includes a sleeve portion 416a and a spring contact portion 416b. The sleeve portion 416a is press fit into or otherwise fixedly mounted within a bore 422a in an extension 422b at the distal end of the second mount portion 422. The spring 414 is positioned about the sleeve portion 416a of the spring retention pin 416 and is interposed between the internal spring engagement member 412c and the spring contact portion 416b for biasing a proximal end 412e of the outer tube 412 toward a distal side wall 422c of the second mount portion 422, see FIGS. 10 and 11.

Three recesses 440a–440c are formed in the extension 422b of the second mount portion 422 and spaced circumferentially apart from one another about the extension 422b, see FIG. 14. The internal position engagement tooth 412d engages with one of the three recesses 440a–440c to lock the wrist 410, and hence, the end effectors 60 and 70, in one of three positions, which are spaced at angles of 0°, 45° and 90°, respectively, to the axis 430, see FIG. 7 and 12. The three recesses 440a–440c are defined by walls 422d and 422e and teeth 422f and 422g on the extension 422b of the second mount portion 422.

A surgeon may change the angular position of the end effectors 60 and 70 prior to inserting the tube 10 into a trocar (not shown) by changing the angular position of the outer tube 412 with respect to the second mount portion 422. This is accomplished by first grasping the outer tube 412 and moving it in a longitudinal direction, denoted by arrow 432, away from the distal side wall 422c of the second mount portion 422 so that the tooth 412d is withdrawn from the recess in which it had been engaged, see FIG. 11. The surgeon then rotates the outer tube 412 to a new desired position and releases the tube 412 so that its proximal end 412e is urged back toward the distal end wall 422c of the second mount portion 422 by the spring 414. As the tube 412 is moved toward the second mount potion 422, the tooth 412d engages with the recess at the new position.

The distal end 412e of the outer tube 412 is provided with an indented mark 412f and the second mount portion 422 is provided with three indented marks 422g–422i. The position of the outer tube 412 relative to the second mount portion 422 can be determined by observing which of the three marks 422g–422i on the second mount portion 422 is positioned across from the mark 412f on the outer tube 412.

As shown in FIGS. 8 and 10–12, the drive cable 50 extends through the wrist 410 and is coupled to the end effectors 60 and 70 via rod end 101 and jaw links 80. Articulation of the end effector portion 400 is effected via knobs 260 and 270 in the same manner discussed above with regard to the first embodiment of the present invention. Rotation of tubes 10 and 20 and drive rod 30 with respect to handle 360 is effected via rotation knob 290 in the same manner set out above with regard to the first embodiment of the present invention.

While, in the illustrated embodiment, three recesses 440a–440c are disclosed, it is contemplated by the present invention that two or more than three recesses may be provided.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A surgical instrument comprising:
   an elongate tubular section including a tubular portion having a distal end and a proximal end and an end effector mount at the distal end of said tubular portion, said end effector mount having first and second mount portions and wrist means associated with and connected to said first and second mount portions for permitting adjustment of the angular position of said first mount portion relative to said second mount portion, said tubular portion being connected to a proximal end of said second mount portion;
   first and second end effectors pivotably connected to a distal end of said first mount portion;
   actuator means connected to said first and second end effectors for effecting pivotable movement of said first and second end effectors; and
   means for effecting pivotable movement of said end effector mount relative to said tubular portion comprising:
   an articulation tube connected at its distal end to a proximal end of said second mount portion; and
   means connected to a proximal end of said articulation tube for reciprocating said articulation tube.

2. A surgical instrument as set forth in claim 1, wherein said end effector mount is pivotably connected to said tubular portion.

3. A surgical instrument as set forth in claim 1, further including means connected to said tubular portion for effecting simultaneous rotation of said first and second end effectors, said end effector mount, and said tubular portion about a longitudinal axis of said tubular portion.

4. A surgical instrument as set forth in claim 1, wherein said actuator means comprises:
   a first handle section connected for pivotable movement relative to a second handle section; and
   means connected to proximal ends of said first and second end effectors and to said first handle section for effecting pivotable movement of said first and second end effectors upon pivotably movement of said first handle section relative to said second handle section.

5. A surgical instrument as set forth in claim 1, wherein said first and second end effectors comprise first and second cutting blades pivotably connected to one another.

6. A surgical instrument comprising:
   an elongate tubular section including a tubular portion having a distal end and a proximal end and an end effector mount at the distal end of said tubular portion, said end effector mount having first and second mount portions and wrist means associated with and connected to said first and second mount portions for permitting adjustment of the angular position of said first mount portion relative to said second mount portion, said tubular portion being connected to a proximal end of said second mount portion;
   first and second end effectors pivotably connected to a distal end of said first mount portion;
   actuator means connected to said first and second end effectors for effecting pivotable movement of said first and second end effectors;
   wherein said wrist means comprises:
   an outer tube fixedly connected to a proximal end of said first mount portion, said outer tube including an internal spring engagement member and an internal position engagement tooth;
   a spring retention pin positioned within said outer tube and including a sleeve portion and a spring contact portion, said sleeve portion being fixedly mounted within a bore in a distal end of said second mount portion;
   a spring positioned about said sleeve portion of said spring retention pin and interposed between said internal spring engagement member and said spring contact portion for biasing a proximal end of said outer tube toward said distal end of said second mount portion; and
   at least first and second recesses formed within said distal end of said second mount portion and spaced circumferentially apart from one another about said distal end of said second mount portion, said outer tube being rotatable about a central axis of said end effector mount between a first position where said position engagement tooth engages with said first recess and a second position where said position engagement tooth engages with said second recess to effect adjustment of the angular position of said first mount portion relative to said second mount portion.

7. A surgical instrument as set forth in claim 6, wherein said internal spring engagement member comprises a snap ring located within an internal circumferential recess in said outer tube.

8. A surgical instrument as set forth in claim 6, wherein said wrist means further includes a third recess formed within said distal end of said second mount portion, said second and third recesses being spaced approximately 45° and 90°, respectively, from said first recess.

9. A surgical instrument comprising:
   an elongate tubular section including a tubular portion having distal and proximal ends and an end effector mount at the distal end of said tubular section having first and second mount portions and wrist means associated with and connected to said first and second mount portions for permitting adjustment of the angular orientation of said first mount portion relative to said second mount portion, said tubular portion being pivotably connected to a proximal end of said second mount portion;
   first and second end effectors pivotably connected to a distal end of said first mount portion;
   actuator means connected to said first and second end effectors for effecting pivotable movement of said first and second end effectors; and
   means for effecting pivotable movement of said end effector mount relative to said tubular portion comprising:
   an articulation tube connected at its distal end to a proximal end of said second mount portion; and
   means connected to a proximal end of said articulation tube for reciprocating said articulation tube.

10. A surgical instrument as set forth in claim 9, further including means connected to said tubular portion for effecting simultaneous rotation of said first and second end effectors, said end effector mount, and said tubular portion about a longitudinal axis of said tubular portion.

11. A surgical instrument as set forth in claim 9, wherein said actuator means comprises:
a first handle section connected for pivotable movement relative to a second handle section; and
means connected to proximal ends of said first and second end effectors and to said first handle section for effecting movement of said first and second end effectors toward and away from one another upon pivotably movement of said first handle section relative to said second handle section.

12. A surgical instrument comprising:
an elongate tubular section including a tubular portion having distal and proximal ends and an end effector mount at the distal end of said tubular section having first and second mount portions and wrist means associated with and connected to said first and second mount portions for permitting adjustment of the angular orientation of said first mount portion relative to said second mount portion, said tubular portion being pivotably connected to a proximal end of said second mount portion;
first and second end effectors pivotably connected to a distal end of said first mount portion;
actuator means connected to said first and second end effectors for effecting pivotable movement of said first and second end effectors;
wherein said wrist means comprises:
an outer tube fixedly connected to a proximal end of said first mount portion, said outer tube including an internal spring engagement member and a position engagement projection;
a spring retention pin positioned within said outer tube and including a sleeve portion and a spring contact portion, said sleeve portion being fixedly mounted within a bore in a distal end of said second mount portion;
a spring positioned about said sleeve portion of said spring retention pin and interposed between said internal spring engagement member and said spring contact portion for biasing a proximal end of said outer tube toward a distal end of said second mount portion; and
at least first and second recesses formed within said distal end of said second mount portion and spaced circumferentially apart from one another about said distal end of said second mount portion, said outer tube being rotatable about a central axis of said end effector mount between a first position where said position engagement projection engages with said first recess and a second position where said position engagement projection engages with said second recess to effect adjustment of the angular orientation of said first mount portion relative to said second mount portion.

13. A surgical instrument as set forth in claim 12, wherein said internal spring engagement member comprises a snap ring located within an internal circumferential recess in said outer tube.

14. A surgical instrument as set forth in claim 12, wherein said wrist means further includes a third recess formed within said distal end of said second mount portion, said second and third recesses being spaced approximately 45° and 90°, respectively, from said first recess.

15. A surgical instrument comprising:
an elongate shaft portion having distal and proximal ends;
an end effector portion connected to the distal end of said shaft portion including an end effector mount having first and second mount portions and wrist means associated with and connected to said first and second mount portions for permitting adjustment of the angular position of said first mount portion relative to said second mount portion, said end effector portion further including first and second end effectors pivotably connected to a distal end of said first mount portion, said shaft portion being connected to a proximal end of said second mount portion;
actuator means connected to said first and second end effectors for effecting pivotable movement of said first and second end effectors; and
means for effecting pivotable movement of said end effector mount relative to said tubular portion comprising:
an articulation tube connected at its distal end to a proximal end of said second mount portion; and
means connected to a proximal end of said articulation tube for reciprocating said articulation tube.

16. A surgical instrument as set forth in claim 15, wherein said shaft portion is pivotably connected to said proximal end of said second mount portion.

* * * * *